United States Patent [19]

Pott

[11] 4,136,550

[45] Jan. 30, 1979

[54] METHOD OF AND DEVICE FOR CHECKING HYGROMETERS AND HYGROSTATS

[75] Inventor: Otto F. Pott, Nurtingen, Fed. Rep. of Germany

[73] Assignee: G. Lufft Metallbarometerfabrik GmbH & Co., Stuttgart, Fed. Rep. of Germany

[21] Appl. No.: 828,612

[22] Filed: Aug. 29, 1977

[30] Foreign Application Priority Data

Sep. 4, 1976 [DE] Fed. Rep. of Germany ....... 2639958

[51] Int. Cl.² ............................................ G01W 1/18
[52] U.S. Cl. .................................................... 73/1 G
[58] Field of Search ................. 73/1 G, 335, 336, 337, 73/337.5

[56] References Cited

U.S. PATENT DOCUMENTS 719,968   2/1903   Wood ...................................... 73/4

OTHER PUBLICATIONS

Wexler et al., Fundamental Techniques for Calibrating Hygrometers, Instrumentation, 1st Quarter 1952, vol. 6, #5, pp. 25, 26 and 27.

Handbook of Physics & Chemistry, 38th Edition 1956–1957, Chemical Rubber Publishing Co., Cleveland, Ohio, pp. 2248, 2249.

Primary Examiner—S. Clement Swisher
Attorney, Agent, or Firm—Walter Becker

[57] ABSTRACT

A method of and device for checking hygrometers and hygrostats, according to which the hygrometer or hygrostat is at its place of mounting checked by means of a reference device, such as a reference hygrometer directly indicating the air humidity. The reference hygrometer is first by means of a corresponding saturated solution calibrated to a standard climate corresponding to the operational climate (Betriebsklima) with regard to the relative humidity, and subsequently at the place of mounting of the device to be checked. The reference hygrometer is together with the hygrometer to be checked exposed to the same conditions. After the reference device has been adapted to the operational conditions (Betriebsbedingungen), the device to be checked is equalized with the reference device.

24 Claims, 5 Drawing Figures

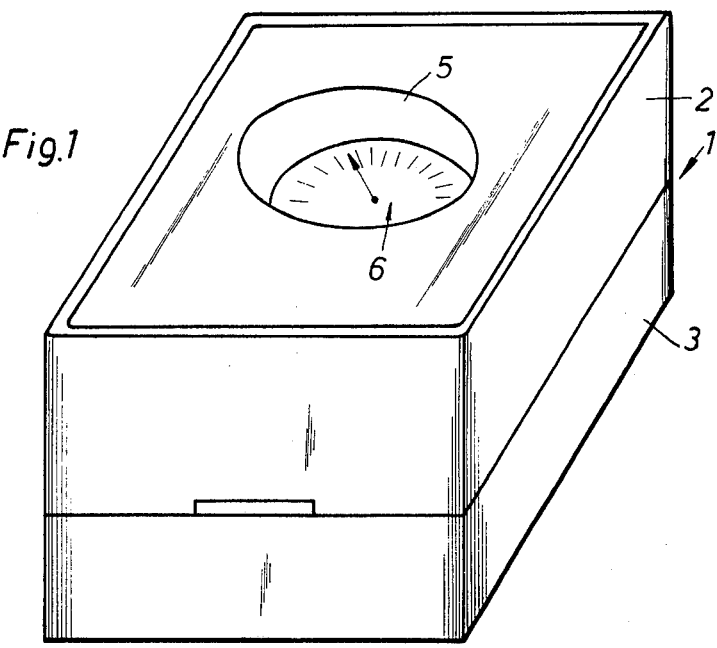
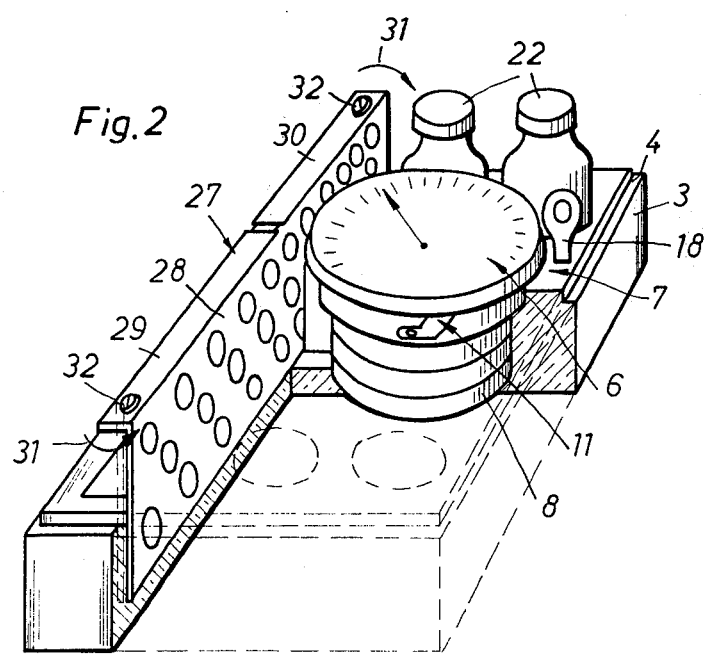

METHOD OF AND DEVICE FOR CHECKING HYGROMETERS AND HYGROSTATS

The present invention relates to a method of and device for checking hygrometers and hygrostats according to which the hygrometers or hygrostats are checked at their respective place by means of a reference device.

Hygrometers and hygrostats which directly indicate the air humidity and which for instance have measuring elements in the form of hair or synthetic elements have to be checked from time to time as to their precision. This is true because in particular, hair generally and also elements of synthetic material post-age or degenerate.

For purposes of checking the operated hygrometers or hygrostats, it was heretofore necessary to remove the same from their place of mounting. This, however, is rather expensive with hygrostats which are electrically connected. Such devices further had to be moved to a normal climate for instance in a room of a corresponding temperature. It is only here that in comparison to said reference climate it could be checked whether the device correctly indicates the temperature and relative humidity. If necessary, a corresponding post-adjustment had to be effected.

While with the above mentioned known method the respective hygrometers or hygrostats had to be removed from their place of mounting, another device is known according to which such removal was not necessary. In this instance, however, so-called psychrometers had to be employed as reference devices at the place of mounting of such hygrometers or hygrostats, for carrying out the comparative measurements. Hygrometers are relatively expensive and complicated and in addition thereto are also awkward to operate. The determination of the air humidity in the last mentioned instance had to be carried out through the detour of measuring the temperature while with two thermometers once the dry temperature and once the temperature with the humidified thermometer is measured. The humidifying results in an evaporation and accordingly in a cooling effect. This in turn brings about a lower temperature indication on the humidity measuring thermometer, while the temperature in this instance comparatively drops all the more the dryer the surrounding air is because with air becoming more and more dry, also the evaporation is increased. From the temperature-difference, a conclusion can be drawn concerning the relative humidity which in practice is effected by conversion tables. The measurement as well as the ascertainment of the result thus contain sources of errors and are not very well suitable for the practice, particularly not for a quick action.

It is, therefore, an object of the present invention to provide a method and device which will make possible the checking of hygrometers and hygrostats in a simple manner and in particular with customary devices at their place of mounting.

These objects and other objects and advantages of the invention will appear more clearly from the following specification in connection with the accompanying drawings, in which:

FIG. 1 is a perspective illustration of a device for checking hygrometers and hygrostats at their place of mounting.

FIG. 2 shows the device according to FIG. 1 with the upper portion of the box containing the devices removed, a portion of the lower section of said box being partly broken open.

Figure 3:
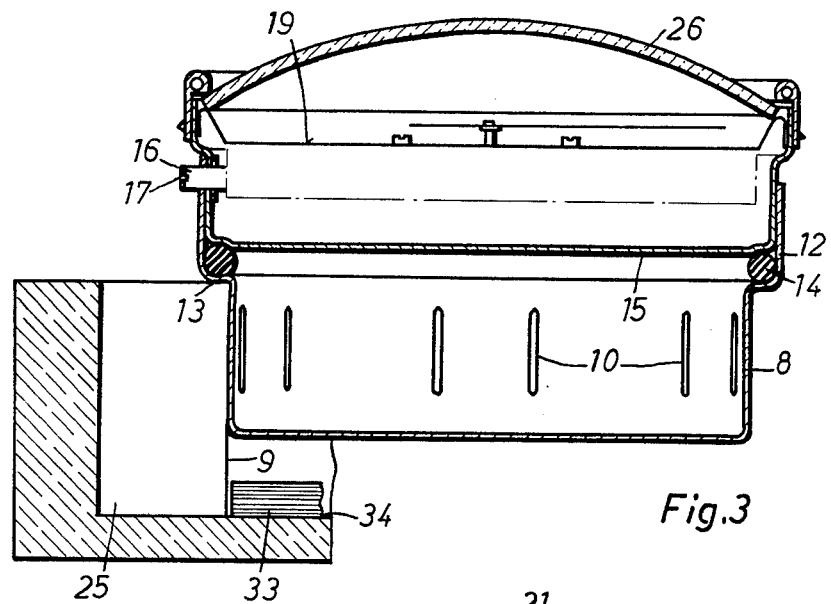
FIG. 3 illustrates in an axial section the hygrometer arranged in the box of the device and furthermore shows an adjacent portion of the lower section of the box.

The method according to the invention for checking hygrometers and hygrostats is characterized primarily in that the hygrometer employed as reference device and directly indicating the air humidity is first by means of a saturated corresponding solution calibrated for a standard or reference climate which corresponds to the respective climate of operation, with regard to the relative humidity, whereupon at the mounting place of the device to be checked, together with the same the device is exposed to the same conditions. The method of the invention is furthermore characterized in that after adapting the reference device to the operational conditions, the device to be checked is equalized with the reference device.

Thus, with the method according to the present invention, first a customary hygrometer which directly indicates the air humidity, for instance as a crosswire hygrometer is exposed to a standard or reference climate and is calibrated thereto if a deviation exists. Subsequently thereto, the thus calibrated hygrometer serving as reference device is moved to the mounting place of the hygrometer which is to be checked and there is exposed to conditions to which also the device to be checked is exposed. After a time of adaptation, the reference device indicates the corresponding measuring value, and now the hygrometer of operation arranged at the mounting place can if necessary be equalized with the values of the reference device. In order to be as close as possible to the prevailing conditions of operation, it is suggested within the ambit of the present invention to select the standard of the reference climate in conformity with the respective climate of operation. This can be realized by the employment of different saturated solutions as calibrating liquids and more specifically for instance lithium chloride for a standard climate with 12% relative humidity, sodium bichromate for a standard climate with 52% relative humidity, sodium chloride for a standard climate of 75.5% of relative humidity and barium chloride for a standard climate of 90% relative humidity. According to whatever is required, within the ambit of the present invention, also other saturated solutions can be employed for other relative values of humidity.

In order during the calibration to assure a constant temperature which is important for precise calibrating values, it has proved expedient according to the invention that the reference device is screened by insulation against its surroundings, at least when the reference device is exposed to the standard climate created by the solution.

According to a further development of the invention, the reference device may after the device to be checked has been equalized, again be exposed to the standard climate created by the solutions, in order in this way to ascertain possible deviations which may have shown up in the meantime, and in order if necessary, to carry out the necessary slight post correction on the device checked in the meantime.

In particular, for carrying out the method according to the invention for checking hygrometers and hygrostats, a device has proved advantageous which comprises a reference device movable to the mounting place while according to the invention the device in addition to comprising a reference device in the form of a hygrometer directly indicating the air humidity also comprises a climate can (Klimadose) at which the hygrometer is to be connected and in which by the introduction of a solution in a manner known per se a standard climate is to be created, said device also comprising a receiving box of insulating material, especially of synthetic material. In the climate can which intentionally as to its size is designed in conformity with the hygrometer and which is so designed that in a simple manner a sealing connection can be established between the hygrometer and the said box, for instance through the intervention of a bayonet joint the standard climate is prior to mounting the hygrometer in customary manner created by introducing into the climate can a paper which is impregnated with a corresponding solution preferably a particularly hygroscopic paper. According to the selection of the respective saturated solution, a standard climate is obtained with a pre-selected relative humidity, and on this relative humidity a calibration of that hygrometer is possible which is employed as reference device. The temperature during the calibration is kept at least nearly constant by the receiving box made of insulating material. In order to be able to carry out the calibration, the box is provided with a sight opening which exposes the scale disc of a hygrometer. The sight opening may within the ambit of the invention comprise a transparent cover associated with the receiving box, on which cover operating instructions may be printed.

In addition to the mentioned sight opening, the receiving box expediently also comprises an access opening for the adjusting screw of the reference device employed as hygrometer in order to be able to carry out a post-adjustment of said reference device without affecting the calibrating conditions.

In addition to the hygrometer insertable as reference device and in addition to the climate can upon which said reference is mountable, the receiving box expediently also receives a plurality of solution containers, especially small bottles, an adjusting tool for the hygrometer as well as moistening material such as hygroscopic paper sheets so that with a receiving box equipped in this way practically a working set is obtained which can easily be carried and which comprises all devices necessary for the checking of hygrometers of hygrostats at the mounting place.

Within the framework of the present invention it is furthermore possible to carry the saturated solvent not separate from the paper sheets but rather to carry said solvent as correspondingly packed and wetted units as for instance impregnated paper sheets packed in aluminum foil. Such pre-packed solvent packs facilitate and speed up the checking work and are also suitable for being dispensed individually or by packs to the final consumer who in this way also obtains the possibility without skill to carry out the necessary post-calibration. Instead of employing saturated solutions of papers impregnated with such solutions, also corresponding salts may be employed.

In particular, in combination with such packed units, there also exists the possibility of exposing the respective device to be checked directly to the standard climate to be created and to carry out the calibration directly on said standard climate.

This expediently also comprises the employment of a mounting device which serves as auxiliary device and by means of which the reference device can be mounted or suspended because said reference device must at the mounting and measuring place be well ventilated in order to avoid faulty indications.

Also this mounting device may within the framework of the present invention be associated with said receiving box while according to the invention there also exists the possibility that with said mounting device and the remaining parts pertaining to said set, a recess is associated in the receiving box. The insertion of the remaining parts as well as of said mounting device into the respective recess can be effected without affecting the outer appearance of the receiving box by dividing the receiving box and by associating the recesses entirely or partially with one or both box sections.

Within the framework of the present invention, the mounting device may in a preferred manner be formed by a U-shaped arc which comprises a foot section, a projecting arm, and therebetween a supporting column interconnecting said foot portion and said projecting arm. The foot portion and projecting arm may expediently be pivotable relative to the supporting column so that the mounting device can be restricted to a rather small space. From a structural standpoint, this can advantageously be realized in a simple manner by forming a foot section, the supporting column, and the projecting arm from angular profiles having a U-shaped cross section, which profiles are pivotally interconnected and the webs of which are located when stretched out substantially in one plane. Thus, assuming a corresponding offset of the arms of the foot portion and the projecting arm relative to the arms of the supporting column, the foot portion and projecting arm can from their inwardly pivoted portion in which the arms of the foot portion and the projecting arm overlap said arms of the supporting column, be pivoted over an angle of 270° into their working position in which the foot portion and projecting arm with the end faces of their webs abut the outside of the web of the supporting column.

According to the present invention, the mounting device may, however, also be designed as frame, and specifically as confining frame for the receiving box, whereby with the corresponding design of the frame, the receiving box is at the same time protected by the mounting device for the transport. To this end, the mounting device may for instance be designed as a closed rectangle which surrounds the receiving box and which by adjusting one or more sides of the mounting device relative to each other is adapted to be braced or clamped relative to the receiving box. Within the framework of the invention, in particular for such mounting device, various design possibilities are open. In particular, a mounting device of the above mentioned shape may have associated therewith a supporting handle for the receiving box.

Referring now to the drawings in detail, the arrangement shown in FIG. 1 illustrates the receiving box 1 comprising an upper section 2 and a lower section 3. Both sections are made of an insulating material, especially a foam synthetic material, preferably polystyrol hard foam material. As will be seen from FIG. 2, these two sections are in positive engagement with each other by means of a rabbet 4 which is shown for the lower section 3 and extends around the edge. Of course, this arrangement may also be reversed which means that the rabbet is in the upper section.

The upper section 2 is provided with a sight opening 5 which is associated with the scale portion 6 of the hygrometer 7 and which may have associated therewith a cover disc not shown in the drawing. FIG. 2 shows for the lower section 3 that the latter has associated therewith recesses for articles pertaining to the receiving box. Correspondingly designed recesses (not shown) may also be provided in the upper section 2. The hygrometer 7 has associated therewith a climate can 8 which is detachably and sealingly connectable to said hygrometer 7 as shown in particular in FIG. 3. From FIG. 3 it will also be seen that the climate can 8 is inserted into a recess 9 of the lower section 3 and more specifically in a fitting manner so that longitudinal ribs 10 provided on the outside on the circumference of the can 8 will when the can 8 is inserted into the lower section 3 positively engage the latter so that an accidental turning of the can 8 relative to the lower section 3 will be prevented. This is important in order to facilitate the placing of the hygrometer 7 which latter may be designed as hairline hygrometer. This prevention of an accidental rotation of the can 8 is particularly important when the connection between climate can 8 and hygrometer 7 is designed as fast closing connection for instance as a bayonet joint 11 shown in FIG. 2. In order to obtain a tight connection when placing the hygrometer 7 upon the climate can 8, the top of the climate can 8 is provided with a widened rim section 12 into which the hygrometer 7 is inserted while in the merging area of said hygrometer with the lower portion of the cam an annular shoulder 13 is provided which serves as support having a sealing ring 14 which may for instance be formed by an O-ring. The sealing ring 14 is when inserting the hygrometer 7 into the can 8 clamped in between the annular shoulder 13 and the bottom 15 of the hygrometer so that a tight connection between can 8 and hygrometer 7 will be assured. This tight connection is necessary in order to be able to build up the desired standard climate in can 8 which standard climate reaches the measuring part of the hygrometer 7 through numerous openings (not shown) provided in the bottom 15.

The measuring part of the hygrometer has not been shown in the hygrometer. As FIG. 3 shows, the measuring part of the hygrometer has associated therewith a radially outwardly projecting adjusting shaft 16 which at its outer end face has a transverse slot 17 for engagement by a screw driver 18. As shown in FIG. 2, said screw driver 18 forms one of the articles pertaining to the receiving box and is arranged in a corresponding recess and easily accessible when taking off the upper section 2.

Figure 4:
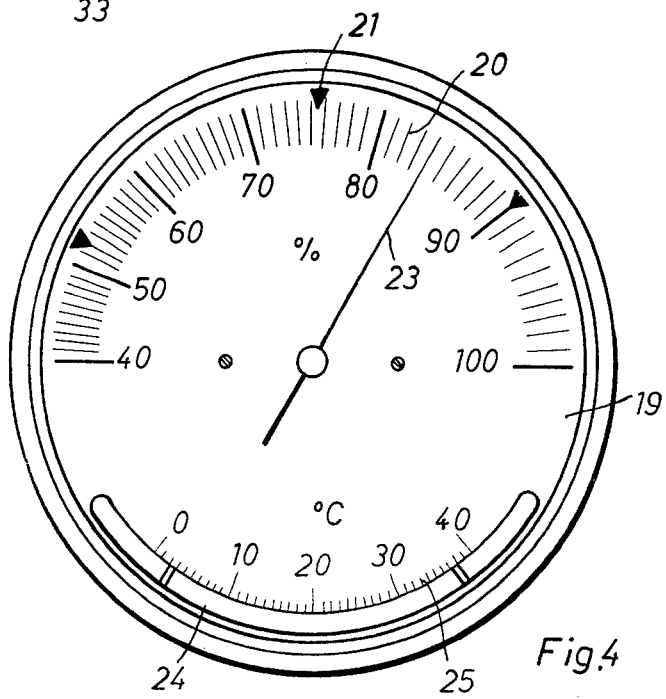
FIG. 4 is a top view of the hygrometer of FIG. 3.

The hygrometer, in customary manner, has a scale disc 19 which with the embodiment of FIGS. 3 and 4 has a scale 20 indicating the relative air humidity. The scale 20 extends over half an arc of the scale disc and may have additional markings 21 for the individual standard climate. If desired, also colored markings may be provided which permit a particularly safe and reliable and confusion-avoiding association of the respective solutions by marking the vessels containing the solutions, especially bottles 22, in the respective same color. These solution bottles are likewise arranged in corresponding recesses of the receiving box. In the particular embodiment shown in the drawing (see FIGS. 1 and 2), these solution containing bottles are, when viewed in the longitudinal direction of the box, arranged on both sides of the hygrometer for two bottles each. In addition to the scale 20 indicating the relative humidity in connection with the pointer 23, the hygrometer as shown in FIGS. 3 and 4 also comprises a mercury thermometer 24 which in the form of an arc is arranged in the region located opposite the scale 20. This thermometer 24 comprises a temperature scale 25. The scale disc 19 with the scales 20 and 25 and pointer 23 associated therewith is covered at the top in customary manner by a clear side disc.

Figure 5:
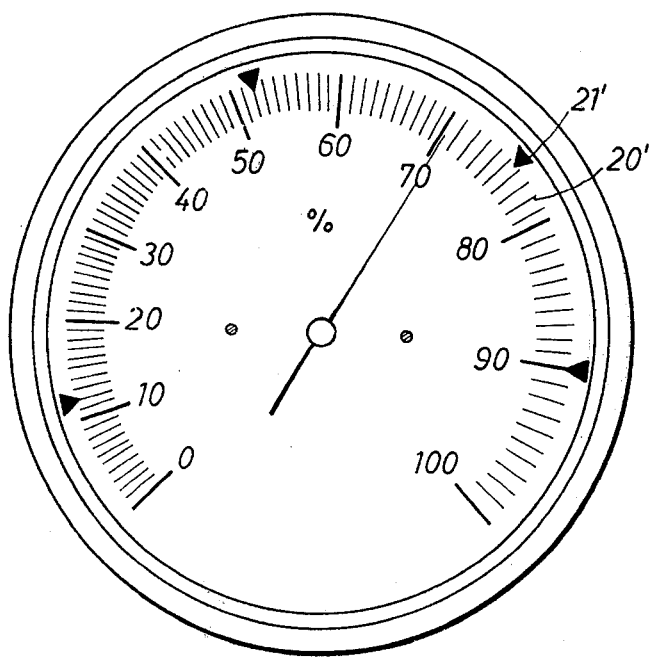
FIG. 5 is a further top view of a hygrometer as it may be arranged in the receiving box, and if desired with an independently provided thermometer which will be insertable into the receiving box from the outside thereof.

Instead of a hygrometer with a scale division according to FIGS. 3 and 4 and an associated thermometer, there may also be provided a hygrometer which comprises an additional measuring and indicating range and in which the scale 20' for indicating the air humidity extends over a larger angle range than in FIG. 4. If such a hygrometer is provided which as to its construction may be similar to that of FIG. 3, a separate thermometer may additionally be provided, preferably in an arrangement which about corresponds to the arrangement of the hygrometer so as to make it possible when employing such hygrometer also to read the air humidity as well as the temperature at any desired time. Also with the hygrometer illustrated in FIG. 5, markings 21 are provided for the individual standard climates. As indicated in connection with FIG. 4, also in this instance colored markings may be provided.

In order to be able after separating the hygrometer which is associated with the receiving box 1 and is employable as reference instrument, after said hygrometer has been separated from the climate can 8, to place said hygrometer at any time at the place of mounting of the operational hygrometer itself, the receiving box has associated therewith a mounting device 27 (FIG. 2). As will be seen from FIG. 2, said receiving device is foldable, and in folded-together position forms a longitudinally extending box body in which the oppositely located longitudinal sides are on one hand formed by the supporting element 20 and on the other hand by the foot portion 29 and the bracket (Kragram) 30 which elements 28, 29 and 30 in the illustrated folded-together position are folded about the supporting element 28. From the illustrated folded-together position, the foot portion 29 and the bracket 30 may as indicated by arrows 31 be pivoted by an angle of 270° and may be brought into an operational position in which the webs of foot portion 29 and bracket 30 rest against the web of the supporting member 28. The supporting member 28, similar to the foot portion 29 and bracket 30 have a U-shaped cross section. From FIG. 2 it will be evident that the foot portion 29 and the bracket 30 are with regard to the supporting member 28 respectively connected within the region of the ends of their webs through pivot axes 32, and that the webs of foot portion 29 and bracket 30 are, as shown for the foot section 29, shortened within the region of the pivot axes 32 relative to the corresponding legs.

FIG. 2 furthermore shows that the supporting element 28, and if desired also the bracket 30, are within the region of the web provided with perforations in order to permit an unimpeded circulation of the air about the hygrometer 7 which is used as reference instrument and is suspended on the mounting device 27. For purposes of suspending the hygrometer 1, preferably in the free end region of the bracket 30, a holding eye or the like may be provided. By means of the mounting device, the reference instrument may also be arranged on the walls, and for suspending the mounting device on the wall, the mounting device may have its supporting member 28 provided with a key-like connecting opening which will assure a simple and safe suspension.

A non-illustrated structural possibility for the supporting device consists in associating the supporting device as frame portion with the receiving box while the supporting device forming a frame section is inserted either into a corresponding recess extending along the circumference of the receiving box, or it is so designed as to extend at least partially around the receiving box in the manner of a surrounding frame. To this end, the mounting device may be formed as a U-shaped surrounding element in which instance the receiving box is inserted into said U-shaped surrounding element and thus forms protective and holding means for the receiving box.

As has been mentioned above, in the climate can by means of pre-determined saturated solution, a standard climate is generated with a corresponding relative air humidity. For introducing the solution into the climate can, paper sheets 33 (FIG. 3) may be employed which are hygroscopic and which are wetted with the respective solution. These paper sheets are provided in larger number and arranged in the receiving box while being located in a recess below the climate can. The withdrawal of the paper sheets 33 from the storage chamber 34 below the climate can 8 is effected by means of a cutout 25 which is arranged adjacent the recess 9 for the climate can and is shown in FIG. 3. The paper sheets may be correspondingly impregnated and may be furnished in packs. Instead of such paper sheets impregnated with saturated solvents, also corresponding salts may be employed.

It is, of course, to be understood that the present invention is, by no means, limited to the specific showing in the drawings, but also comprises any modifications within the scope of the appended claims.

What I claim is:

1. A device for checking instruments such as hygrometers and hygrostats at their place of mounting, which includes: a reference instrument of the same type as the instrument to be checked and operable directly to indicate the air humidity, a climate can connectable to said reference instrument and operable to receive an appropriate solution for creating a standard climate, and a receiving box of insulating material having said reference instrument and said climate can arranged therein.

2. A device according to claim 1, in which said insulating material is foamed synthetic material.

3. A device according to claim 1, in which said solution is selected from the group consisting of lithium chloride for a standard climate with 12% relative humidity, sodium bicarbonate for a standard climate with a 52% relative humidity, sodium chloride for a standard climate with a 75.5% relative humidity, and barium chloride for a standard climate with a 90% relative humidity.

4. A device according to claim 1, which includes means adapted to receive said solution and associated with said receiving box.

5. A device according to claim 4, in which said means for receiving said solution comprises a paper sheet impregnated with said solution.

6. A device according to claim 4, in which said means for receiving said solution comprises a packet containing a salt of said solution.

7. A device according to claim 1, which includes an adjusting tool for adjusting said reference instrument.

8. A device according to claim 1, which includes humidifying material arranged in said receiving box.

9. A device according to claim 8, in which said humidifying material includes hygroscopic paper sheets.

10. A device according to claim 1, which includes mounting means for said reference instrument, said mounting means including a bracket section foldable with said receiving box.

11. A device according to claim 1, in which said receiving box comprises an upper section and a lower section separable from each other, said sections having interengaging portions, at least one of said sections including recess means sealed toward the outside.

12. A device according to claim 1, in which said receiving box has a sight opening, and in which said reference instrument has a scale disc readable through said sight opening.

13. A device according to claim 10, in which said mounting means including said bracket section are adapted to be folded together.

14. A device according to claim 13, in which said mounting means has said foot section, a supporting section, and a bracket section.

15. A device according to claim 14, in which said foot section and said bracket section are foldable collectively from an unfolded position specifically toward said supporting section.

16. A device according to claim 15, in which said foot section and said bracket section are foldable from their unfolded position toward said supporting section by turning about an angle of about 270°.

17. A device according to claim 16, in which each of said foot sections and said bracket section and said supporting section leave a U-shaped cross sectional profile the webs of which in unfolded position of said foot section and said bracket section are about aligned with each other and with said supporting section.

18. A device according to claim 17, in which said mounting means form a frame associated with said receiving box.

19. A device according to claim 18, in which said frame extends specifically at least over two sides of said receiving box.

20. A device according to claim 19, in which said mounting means forms a closed frame.

21. A device according to claim 20, in which said frame forms a portion of the outside of said device.

22. A device according to claim 21, in which said mounting means is provided with a handle.

23. A device according to claim 22, in which said frame has an opening forming said handle.

24. A method of checking calibration of instruments used for relative humidity purposes including a hygrometer and a hygrostat, comprising in combination the steps of: checking the instrument to be checked by a reference instrument of the same type operable to directly indicate the air humidity and confined in an insulation medium to maintain a constant temperature, calibrating said reference instrument by means of a corresponding saturated solution associated with said reference instrument in said insulation medium to a standard climate corresponding to the operational climate with regard to the relative humidity, maintaining said reference instrument and said saturated solution in said insulation and subsequently at the place of mounting of the instrument to be checked exposing said reference instrument together with the hygrometer to be checked to the same conditions, and after the reference instrument has been adapted to the operational conditions, equalizing the instrument to be checked with said reference instrument, during the calibration of said reference instrument exposing the latter to the standard climate created by said solution while during said calibration insulating said reference instrument with regard to its surrounding, following the equalization of the instrument to be checked again exposing said reference instrument to the standard climate created by said solution and confined in said insulation medium, said solution being selected from the group consisting of lithium chloride for a standard climate with a 12% relative humidity, sodium bichromate for a standard climate with a 52% relative humidity, sodium chloride for a standard climate with a 75.5% relative humidity, and barium chloride for a standard climate with a 90% relative humidity.

* * * * *